United States Patent
Röder et al.

(10) Patent No.: US 7,709,409 B2
(45) Date of Patent: May 4, 2010

(54) MIXED CATALYTIC COMPOSITION

(75) Inventors: Jens Röder, Frankfurt am Main (DE);
Andrea Kapries, Herbern (DE);
Thorsten Nordhorn, Kamen (DE);
Johannes Canisius, Bochum (DE)

(73) Assignee: Chemtura Organometallics GmbH, Bergkamen (DE)

( * ) Notice: Subject to any disclaimer, the term of this patent is extended or adjusted under 35 U.S.C. 154(b) by 0 days.

(21) Appl. No.: 11/784,492

(22) Filed: Apr. 6, 2007

(65) Prior Publication Data

US 2007/0179045 A1    Aug. 2, 2007

Related U.S. Application Data

(63) Continuation of application No. 10/536,869, filed as application No. PCT/EP03/13222 on Nov. 25, 2003, now abandoned.

(30) Foreign Application Priority Data

Nov. 29, 2002    (DE) ................. 102 56 084

(51) Int. Cl.
*B01J 31/00*    (2006.01)
*C08G 63/00*    (2006.01)

(52) U.S. Cl. ............ 502/155; 528/272; 528/274; 502/110; 502/111; 502/150

(58) Field of Classification Search ............. 502/110, 502/111, 150, 155; 528/272, 274
See application file for complete search history.

(56) References Cited

U.S. PATENT DOCUMENTS

2002/0052462 A1    5/2002   Masuda et al.
2003/0149226 A1*   8/2003   Conrad et al. ............... 528/283

FOREIGN PATENT DOCUMENTS

GB    1338091 A      11/1973
JP    55-142024   *  11/1980
JP    6-248060 A     9/1994

OTHER PUBLICATIONS

International Preliminary Examination Report regarding International Application No. PCT/EP 03/13222.
International Search Report regarding International Application No. PCT/EP 03/13222.

* cited by examiner

*Primary Examiner*—Milton I Cano
*Assistant Examiner*—Gennadiy Mesh
(74) *Attorney, Agent, or Firm*—JoAnn Villamizar

(57) ABSTRACT

The present invention relates to catalytic compositions for esterification, transesterification and polycondensation reactions, a process for the catalysis of said reactions employing such catalytic compositions and polyesters or resins obtainable by this process.

3 Claims, No Drawings

MIXED CATALYTIC COMPOSITION

This application is a continuation of U.S. patent application Ser. No. 10/536,869, filed May 27, 2005, now abandoned which is a national stage of PCT/EP03/13222 filed Nov. 25, 2003 and each of the above is incorporated by reference in there entireties herein.

The present invention relates to catalytic compositions for esterification, transesterification and polycondensation reactions, a process for the catalysis of said reactions employing such catalytic compositions and polyesters or resins obtainable by this process.

Catalytic systems containing organotin compounds are widely known. JP-A 06-248060, JP-A 03-284414 and JP-A 03-218511 describe catalyst systems based on organo tin compounds and trivalent and pentavalent heteroatom compounds especially phosphorous ligands, used in the ring opening polymerization of lactides. These systems are used to optimize the mechanical and thermal resistance of the polymer.

The application of such catalytic compositions for carrying out or accelerating other reactions has not been reported so far.

In contrast, DE-A-101 21 542 reports further that e.g. stabilizers containing heteroatoms are used for quenching the catalyst within the esterification, transesterification or pre-condensation step as these compounds form inactive products together with the catalyst.

Furthermore, special processes are known in which defined catalyst and stabilizer concentrations and defined locations for their addition are used. Herein the stabilizer is added after the catalyst. According to DE-A-19 50 997 it is common to deactivate the transesterification catalyst with a suited amount of a trivalent or pentavalent heteroatom containing compound by coordination or covalent bonding. This is done to avoid a detrimental influence of the transesterification catalyst within the polycondensation reaction. The polycondensation catalyst is added after this deactivation, a further polycondensation stabilizer might be added later.

Furthermore is known that during the production of polyesters for some applications for example wrappings and technical yarns, a crystallization and polycondensation in the solid state is carried out (U.S. Pat. Nos. 4,064,112, 4,263,425, 5,362,844). In other applications, fibers or filaments are spun directly and direct preforms are produced in a process wherein an intermediate transfer into the solid state and a repeated remelting is not applied.

Conventional polyester compositions are connected with a series of disadvantages (general summary in: Handbook of polyester thermoplastics, 1st edition, Wiley-VCH, Weinheim, 2002). Among these disadvantages are in particular:

Necessity of high temperatures for the synthesis

High catalyst concentration (100-500 ppm [as metal])

Degradation processes under processing and polycondensation conditions; for example formation of vinyl esters and due to the formation of acetic aldehyde in polyethylene terephthalate (PET), formation of acrolein in polypropylene terephtalate (PPT) and tetrahydrofuran formation in polybutylene terephthalate (PBT).

Limited use of the catalyst systems, dependent on the technology of the process and the chemical structure of the substrate; classic titanium based catalysts cannot be added for example during the esterification- and/or pre/condensation step, as these are readily hydrolyzed to inactivate titanium oxides.

Application of the catalyst system only in selected process stages for example only during the esterifications- or only during the transesterification- or only during the polycondensation stage.

Optical turbidity of the produced polyester for example by deposits of elementary metal impurities as this can occur by the use of antimony based catalyst systems.

Discoloration of the polyester by the catalyst itself, for example titanium based catalyst systems cause a yellow coloring of the polymer or formation of chromophor by-products, respectively.

Problematic metering and addition of catalysts and catalyst formulations.

Object of the present invention is to provide a catalytic composition, suitable for catalyzing esterification, transesterification and poly-condensation reactions, an improved process of esterification, trans-esterification and polycondensation reactions and the production of improved polyesters for bottles, films, foils, yarn, molded padding, resins for powder coatings and technical synthetic materials, which avoid the disadvantages of the prior art.

The catalytic composition for esterification, transesterification and polycondensation reactions according to the invention contains a mixture of at least one organotin compound (compound I) of the general formula (I):

(formula I)

wherein

R1 is selected from the group of linear, branched or cyclic alkyl groups having 1 to 40 carbon atoms, aryl groups having 1 to 40 carbon atoms, or substituents selected from the group: —X—$R^A$, wherein $R^A$ is —CN, —COOH, —COO-methyl, —COO-ethyl, —COO-n-propyl, —COO-iso-propyl, —COO-n-butyl, —COO-2-butyl, —COO-iso-butyl, —COO-tert-butyl, —COO-n-pentyl, —COO-isopentyl, —COO-neo-pentyl, —COO-tert-pentyl, —COO-hexyl, —COO-heptyl, —COO-n-octyl, —COO-iso-octyl, —COO-2-ethyl-1-hexyl, —COO-2,2,4-trimethylpentyl, —COO-nonyl, —COO-decyl, —COO-dodecyl, —COO-n-dodecyl, —COO-cyclopentyl, —COO-cyclohexyl, —COO-cycloheptyl, —COO-methylcyclohexyl, —COO-vinyl, —COO-1-propenyl, —COO-2-propenyl, —COO-naphtyl, —COO-anthranyl, —COO-phenanthryl, —COO-o-tolyl, —COO-p-tolyl, —COO-m-tolyl, —COO-tolyl, —COO-ethylphenyl, —COO-mesityl, —COO-benzyl, —COO-phenyl, —COO$C_2H_4$OH, —COO$C_3H_6$OH, —COO$C_4H_8$OH, —COO$CH_2C(CH_3)_2CH_2$OH; and —X— is —$CH_2$—, —$C_2H_4$—, —$C_3H_6$—, —$C_4H_8$—, —$C_5H_{10}$—, or —$C_6H_{12}$—;

R2 is selected from the groups of linear, branched or cyclic alkyl groups having 1 to 40 carbon atoms, aryl groups having 1 to 40 carbon atoms and anionic ligands with O-coordination of the group selected from —O, —OH, linear, branched or cyclic alkyl or arylcarboxy groups having 1 to 40 carbon atoms, linear, branched or cyclic alkyl-, and aryl alcoholate groups having 1 to 40 carbon atoms;

R3 and R4 independently each are selected from the groups of anionic ligands with O-coordination of the group selected from —O, —OH, linear, branched or cyclic alkyl groups or arylcarboxy groups having 1 to 40 carbon atoms, linear, branched or cyclic alkyl-, and aryl alcoholate groups having 1 to 40 carbon atoms and anions of a mineral acid selected from the group of sulphate, sulphite, phosphate, halogen- or pseudohalogen anion and at least one compound (compound II) according to one of the formulae (II), (III) and/or (IV), $$X_m(R')_n \quad \text{(Formula II)}$$

$$O=X_m(R')_o \quad \text{(Formula III)}$$

$$(O=)_r X_m O_p(R')_q \quad \text{(Formula IV)}$$

wherein X is a heteroatom selected from the group consisting of N, P, Si, Cl, Br, I or S, m is an integer from 1 to 5,
n is an integer from 1 to 5,
o is an integer from 1 to 5,
p is an integer from 0 to 5,
q is an integer from 0 to 5,
r is an integer from 0 to 3, wherein R' in formula (II) denotes n different or identical groups, each being independent from each other selected from the group of linear, branched or cyclic alkyl groups having 1 to 40 carbon atoms, aryl groups having 1 to 40 carbon atoms, anionic ligands with O-coordination selected from the group of —O, —OH, linear, branched or cyclic alkyl-, and aryl alcoholate groups having 1 to 40 carbon atoms, H, Cl, Br, $NH_4^+$ or a metal ion, R' in formula (III) denotes o different or identical groups, each being independent from each other selected from the group of linear, branched or cyclic alkyl groups having 1 to 40 carbon atoms, aryl groups having 1 to 40, anionic ligands with O-coordination selected from the group of —O, —OH, linear, branched or cyclic alkyl-, and arylalcoholate groups having 1 to 40 carbon atoms, H, Cl, Br, $NH_4^+$ or a metal ion, R' in formula (IV) denotes q different or identical groups, each being independent from each other selected from the group of linear, branched or cyclic alkyl groups having 1 to 40 carbon atoms, aryl groups having 1 to 40, anionic ligands with O-coordination selected from the group of —O, —OH, linear, branched or cyclic alkyl-, and arylalcoholate groups having 1 to 40 carbon atoms, H, Cl, Br, $NH_4^+$ or a metal ion.

Said catalytic compositions proved highly effective in the catalysis of esterification, transesterification, polycondensation, polyesterification and polytransesterification reactions.

It has to be pointed out that according to the invention compound I and compound II form a physical mixture and do not chemically react with each other. That means compound I and compound II are neither connected by a complex nor a covalent bond. For example, in the case that compound II is a phosphorous compound this is confirmed by the $^{31}P$ NMR data of the physical mixture of compound I and compound II.

Preferred metal ions according to the invention include $NH_4$, Li, Na, K, Rb, Cs, Mg, Ca, Sr, Ba, Zn, B, Al, Sc, Y.

Preferred examples for compound I are defined by R1=methyl, ethyl, n-propyl, iso-propyl, n-butyl, 2-butyl, iso-butyl, tert-butyl, n-pentyl, iso-pentyl, neo-pentyl, tert-pentyl, hexyl, heptyl, n-octyl, iso-octyl, 2-ethyl-1-hexyl, 2,2,4-trimethylpentyl, nonyl, decyl, dodecyl, n-dodecyl, cyclopentyl, cyclohexyl, cycloheptyl, methylcyclohexyl, vinyl, 1-propenyl, 2-propenyl, naphthyl, anthranyl, phenanthryl, o-tolyl, p-tolyl, m-tolyl, xylyl, ethylphenyl, mesityl, phenyl, benzyl, or R1 a substituent from the group: —X—$R^A$ with $R^A$=—CN, —COOH, —COO-methyl, —COO-ethyl, —COO-n-propyl, —COO-iso-propyl, —COO-n-butyl, —COO-2-butyl, —COO-iso-butyl, —COO-tert-butyl, —COO-n-pentyl, —COO-isopentyl, —COO-neo-pentyl, —COO-tert-pentyl, —COO-hexyl, —COO-heptyl, —COO-n-octyl, —COO-iso-Octyl, —COO-2-Ethyl-1-hexyl, —COO-2,2,4-trimethylpentyl, —COO-nonyl, —COO-decyl, —COO-dodecyl, —COO-n-dodecyl, —COO-cyclopentyl, —COO-cyclohexyl, —COO-cycloheptyl, —COO-methylcyclohexyl, —COO-Vinyl, —COO-1-propenyl, —COO-2-propenyl, —COO-naphtyl, —COO-anthranyl, —COO-phenanthryl, —COO-o-tolyl, —COO-p-tolyl, —COO-m-tolyl, —COO-xylyl, —COO-ethylphenyl, —COO-mesityl, —COO-benzyl, —COO-phenyl, —$COOC_2H_4OH$, —$COOC_3H_6OH$, —$COOC_4H_8OH$, —$COOCH_2C(CH_3)_2CH_2OH$; with —X—: —$CH_2$—, —$C_2H_4$—, —$C_3H_6$—, —$C_4H_8$—, —$C_5H_{10}$—, —$C_6H_{12}$—.

Especially preferred substituents according to the invention are: methyl, n-butyl, n-octyl und n-dodecyl.

According to the invention —X— is preferably —$C_2H_4$—, and preferred moieties $R^A$ are —CN, —COOH, —COO-methyl, —COO-ethyl.

Preferred examples for R2 are according to the invention:

a) methyl, ethyl, n-propyl, iso-propyl, n-butyl, 2-butyl, iso-butyl, tert-butyl, n-pentyl, iso-pentyl, neo-pentyl, tert-pentyl, hexyl, heptyl, n-octyl, iso-octyl, 2-ethyl-1-hexyl, 2,2,4-trimethylpentyl, nonyl, decyl, dodecyl, n-dodecyl, cyclopentyl, cyclohexyl, cycloheptyl, methylcyclohexyl, vinyl, 1-propenyl, 2-propenyl, naphthyl, anthranyl, phenanthryl, o-tolyl, p-tolyl, m-tolyl, xylyl, ethylphenyl, mesityl, phenyl, benzyl. Favored substituents for the invention are: Methyl, butyl, octyl and dodecyl, or b) O, OH, methanolate, ethanolate, n-propanolate, iso-propanolate, n-butanolate, 2-butanolate, iso-butanolate, tert-butanolate, n-pentanolate, iso-pentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclopentanolate, cyclohexanolate, cycloheptanolate, methylcyclohexanolate, glycolate, glycerate, pinacolate neopentylglycolate, vinylalcoholate, propargylalcoholate, 2-ethyl-1-hexanolate, formiate, acetate, propionate, butyrate, valeriate, caprate, caprylate, caprinate, laurate, laureate, 2-ethyl-1-hexanoate, neodecanoate, palmitate, stearate, benzoate, terephthalate, phthalate, isoterephthalate, acrylate, methacrylate, crotonate, isocrotonate, vinylacetate, oleate, sorbate, linolate, linolenate, trifluoracetate, p-toluolsulfonate, oxalate, malonate, succinate, glutarate, adipate, fumarate, maleinate, carboxylates of the following monoesters: methylmaleicacid monoester, ethylmaleicacid monoester, butyl-maleicacid monoester, n-propylmaleicacid monoester, iso-propyl-maleicacid monoester, n-butylmaleicacid monoester, 2-butyl-maleicacid monoester, iso-butylmaleicacid monoester, tert-butylmaleicacid monoester, n-pentylmaleicacid monoester, isopentylmaleicacid monoester, neo-pentylmaleicacid monoester, tert-pentylmaleicacid monoester, 2-methyl-1-butylmaleicacid monoester, hexylmaleicacid monoester, heptylmaleicacid monoester, n-octylmaleicacid monoester, iso-octylmaleicacid monoester, 2,2,4-trimethylpentylmaleicacid monoester, nonylmaleicacid monoester, decylmaleicacid monoester, dodecylmaleicacid monoester, n-dodecylmaleicacid monoester, cyclopentylmaleicacid monoester, cyclohexylmaleicacid monoester, cycloheptylmaleicacid monoester, methylcyclohexylmaleicacid monoester, glycolmaleicacid monoester, glycerolmaleicacid monoester, pinakolmaleicacid monoester, neopentylglycolmaleicacid monoester, vinylmaleicacid monoester, propargylmaleicacid monoester and 2-ethyl-1-hexylmaleicacid monoester, citrate, lactate, tartrate, naphtenate, naphthalen-2,6-dicarboxalate, naphthalene-1,6-dicarboxalate, F, Cl, ClO, $ClO_2$, $ClO_3$, $ClO_4$, Br, J, CN, SCN, OCN, sulphate, hydrogensulphate, sulphite, hydrogensulphite, sulphide, phosphate, hydrogenphosphate, dihydrogenphosphate, bis(2-ethyl-1-hexyl)phosphate, butylphosphate, dibutylphosphate, 3-phosphonopropionate, phenylphosphonacid, benzolphosphonigacid, p-aminophosphonacid, n-octylphosphonacid favored substituents are: O, OH, laureate, 2-ethyl-1-hexanoate, neodecanoate, oxalate, 2-ethyl-1-hexylmaleicacid monoester and acetate.

Preferred examples for R3 and R4 are according to the invention : O, OH, methanolate, ethanolate, n-propanolate, iso-propanolate, n-butanolate, 2-butanolate, iso-butanolate, tert-butanolate, n-pentanolate, iso-pentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclopentanolate, cyclohexanolate, cycloheptanolate, methylcyclohexanolate, glycolate, glycerate, pinacolate neopentylglycolate, vinylalcoholate, propargylalcoholate, 2-ethyl-1-hexanolate, formiate, acetate, propionate, butyrate, valeriate, caprate, caprylate, caprinate, laureate, 2-ethyl-1-hexanoate, neodecanoate, palmitate, stearate, benzoate, terephthalate, phthalate, isoterephthalate, acrylate, methacrylate, crotonate, isocrotonate, vinylacetate, oleate, sorbate, linolate, linolenate, trifluoracetate, p-toluolsulfonate, oxalate, malonate, succinate, glutarate, adipate, fumarate, maleinate, methylmaleicacid monoester, ethylmaleicacid monoester, butylmaleicacid monoester, n-propylmaleicacid monoester, iso-propylmaleicacid monoester, n-butylmaleicacid monoester, 2-butylmaleicacid monoester, iso-butylmaleicacid monoester, tert-butylmaleicacid monoester, n-pentylmaleicacid monoester, isopentylmaleicacid monoester, neo-pentylmaleicacid monoester, tert-pentylmaleicacid monoester, 2-methyl-1-butylmaleicacid monoester, hexylmaleicacid monoester, heptylmaleicacid monoester, n-octylmaleicacid monoester, iso-octylmaleicacid monoester, 2,2,4-trimethylpentylmaleicacid monoester, nonylmaleicacid monoester, decylmaleicacid monoester, dodecylmaleicacid monoester, n-dodecylmaleicacid monoester, cyclopentylmaleicacid monoester, cyclohexylmaleicacid monoester, cycloheptylmaleicacid monoester, methylcyclohexylmaleicacid monoester, glycolmaleicacid monoester, glycerolmaleic acid monoester, pinacolmaleicacid monoester, neopentylglycolmaleicacid monoester, vinylmaleicacid monoester, propargylmaleicacid monoester and 2-ethyl-1-hexylmaleicacid monoester, citrate, lactate, tartrate, naphtenate, naphthalene-2,6-dicarboxalate, naphthalene-1,6-dicarboxalate, F, Cl, ClO, $ClO_2$, $ClO_3$, $ClO_4$, Br, J, CN, SCN, OCN, sulphate, hydrogensulphate, sulphite, hydrogensulphite, sulphide, phosphate, hydrogenphosphate, dihydrogenphosphate, bis (2-ethyl-1-hexyl)phosphate, butylphosphate, dibutylphosphate, 3-phosphonopropionate, phenylphosphonacid, benzoenephosphonigacid, p-aminophosphonacid, n-octylphosphonacid. Most preferred substituents are: O, OH, Cl, laureate, 2-ethyl-1-hexanoate, neodecanoate, oxalate, 2-ethyl-1-hexylmaleicacid monoester and acetate.

Preferred examples for compound II of the invention are phosphites, phosphines, phosphonic acid esters, pyrophosphates, alkaline halogenides, earth alkaline halogenides, aluminum halogenides.

According to the invention combinations with the following examples of compound II are particularly preferred: Formula II (X=P): trioctyl-, triisooctyl-, trilauryl, tridecyl-, tridodecyl-, triisododecyl-, tritridecyl-, tripentadecyl-, trioleyl, tristearyl-, triphenyl-, trikresyl-, tris-nonylphenol, tris-2,4-t-butyl-phenyl- or tricyclohexylphosphite.

Further preferred phosphites of several aryl-dialkyl or alkyl-diarylphosphite may be advantageously applied, such as phenyldi-octyl-, phenyididecyl-, phenyldidodecyl-, phenyldidtridecyl-, phenyiditetradecyl-, phenyldipentadecyl-, octyldiphenyl-, decycddiphenyl-, undecyidiphenyl-, dodecyldiphenyl-, tridecyldiphenyl-, tetradecyldiphenyl-, pentadecyldiphenyl-, oleyldiphenyl-, stearyidiphenyl- und dodecyl-bis-2,4-di-t-butylphenylphosphite, tris(2,4-di-tert-butylphenyl)phosphite, diphenylisodecylphosphite.

Also phosphites of several di- or polyols are very well suited and therefore preferred, e.g. phenylneopentylenglycolphosphite, heptakis-(dipropyleneglycol)triphosphite, 2,4,6-tri-tert-butylphenyl-2-butyl-2-ethyl-1,3-propandiolphosphite, bis(2,4-tri-tert-butylphenyl)pentaerythritoldiphosphite, tetraphenyldipropylenglykoldiphosphite, polydi-propyleneglykolphenylphosphite, tetramethylol-cyclohexanol-decyldi-phosphite, tetramethylolcyclohexanol-butoxyethoxyethyldiphosphite, tetramethylolcyclohexanol-nonylphenyldiphosphite, bis-nonylphenyl-di-trimethylolpropanediphosphite, bis-2-butoxyethyl-di-trimethylol-propanediphosphite, trishydroxyethylisocyanurat-hexadecyltriphosphite, tris (dipropyleneglycol)phosphite, poly-4,4'-isopropylidendiphenol-c12-15-alcoholphosphite, diisodecylpentaerythritol-diphosphite, didecylpenta-erythritdiphosphite, distearylpentaerythritdiphosphite, also mixtures of these phosphites and aryl/alkylphbsphite-mixtures of the statistic composition $(H_{19}C_9—C_6H_4)O_{1,5}P(OC_{12,13}H_{25,27})_{1,5}$ or $[C_8H_{17}—C_6H_4—O—]_2P[i-C_8H_{17}O](H_{19}C_9—C_6H_4)O_{1,5}P(OC_{9,11}H_{19,23})_{1,5}$ are suitable as well as phosphines with R1', R2', R3'=methyl, ethyl, n-propyl, iso-propyl, n-butyl, 2-butyl, iso-butyl, tert-butyl, n-pentyl, isopentyl, neo-pentyl, tert-pentyl, hexyl, heptyl, n-octyl, iso-octyl, 2,2,4-trimethylpentyl, nonyl, decyl, dodecyl, n-dodecyl, cyclopentyl, cyclohexyl, cycloheptyl, methylcyclohexyl, o-tolyl, p-tolyl, m-tolyl, xylyl, ethylphenyl, mesityl, phenyl, benzyl and also DIOP, Chiraphos and Norphos.

According to the invention especially favored are heteroatom compounds II including heteroatoms such as according to formula II wherein R1', R2' and R3' are each independently selected from $C_6H_5$, $OC_6H_5$ and $OC_4H_9$.

Moreover, according to the invention mixtures of compound I with a compound II according to formula III are particularly preferred, such as e.g. (X=P): R1', R2', R3'=Methyl, ethyl, n-propyl, iso-propyl, n-butyl, 2-butyl, iso-butyl, tert-butyl, n-pentyl, iso-pentyl, neo-pentyl, tert-pentyl, hexyl, heptyl, n-octyl, iso-octyl, 2,2,4-trimethylpentyl, nonyl, decyl, dodecyl, n-dodecyl, cyclopentyl, cyclohexyl, cycloheptyl, methylcyclohexyl, vinyl, 1-propenyl, 2-propenyl naphthyl, anthryl, phenanthryl, o-tolyl, p-tolyl, m-tolyl, xylyl, ethylphenyl, mesityl, phenyl, benzyl, methanolate, ethanolate, n-propanolate, iso-propanolate, n-butanolate, 2-butanolate, iso-butanolate, tert-butanolate, n-pentanolate, isopentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclopentanolate, cyclohexanolate, cycloheptanolate, methylcyclohexanolate, glycolate, glycerate, pinacolate, neopentylglycolate, vinylalcoholate, propargylalcoholate, 2-ethyl-1-hexanolate, ethyleneglycol, diethyleneglycol, triethyleneglycol und benzylalcoholate and for X=2: tetramethylpyrophosphate, tetra ethylpyrophosphate, tetrakis-n-propylpyrophosphate, tetrakis-iso-propyl pyrophosphate, tetrakis-n-butylpyrophosphate, tetrakis-2-butylpyro-phosphate, tetrakis-iso-butylpyrophosphate, tetrakis-tert-butylpyro-phosphate, tetrakis-n-pentylpyrophosphate, tetrakis-iso-pentylpyro-phosphate, tetrakis-neo-pentylpyrophosphate, tetrakis-tert-pentylpyro-phosphate, tetrahexylpyrophosphate, tetraheptylpyrophosphate, tetrakis-n-octylpyrophosphate, tetrakis-iso-octylpyrophosphate, tetrakis-2-ethyl-1-hexylpyrophosphate, tetrakis-2,2,4-trimethylpentyl-pyrophosphate, tetranonylpyrophosphate, tetradecylpyrophosphate, tetradodecylpyrophosphate, tetrakis-n-dodecylpyrophosphate, tetra-cyclopentylpyrophosphate, tetracyclohexylpyrophosphate, tetracyclo-heptylpyrophosphate, tetrakis-methylcyclohexylpyrophosphate, tetranaphthylpyrophosphate, tetraanthrylpyrophosphate, tetraphenanthryl-pyrophosphate, tetrakis-o-tolylpyrophosphate, tetrakis-p-tolylpyro-phosphate, tetrakis-m-tolylpyrophosphate, tetraxylylpyrophosphate, tetrakis-ethylphenylpyrophosphate, tetramesitylpyrophosphate, tetraphenylpyrophosphate, tetrabenzylpyrophosphate or R1', R2'=Methyl, ethyl, n-propyl, iso-propyl, n-butyl, 2-butyl, iso-butyl, tert-butyl, n-pentyl, isopentyl, neo-pentyl, tert-pentyl, hexyl, heptyl, n-octyl, iso-octyl, 2,2,4-trimethylpentyl, nonyl, decyl, dodecyl, n-dodecyl, cyclopentyl, cyclohexyl, cycloheptyl, methylcyclohexyl, vinyl, 1-propenyl, 2-propenyl naphtyl, anthryl, phenanthryl, o-tolyl, p-tolyl, m-tolyl, xylyl, ethylphenyl, mesityl, phenyl, benzyl, methanolate, ethanolate, n-propanolate, iso-propanolate, n-butanolate, 2-butanolate, iso-butanolate, tert-butanolate, n-pentanolate, isopentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclo-pentanolate, cyclohexanolate, cycloheptanolate, methylcyclohexanolate, glycolate, glycerate, pinacolate neopentylglycolate, vinylalcoholate, propargylalcoholate, 2-ethyl-1-hexanolate, ethylenglycol, diethylene-glycol, triethylenglycol and benzylalcoholate, R3'=H such as e.g. diphenylphosphite. Triphenylphosphinoxide, triethylphosphate, tributyl-phosphate, triphenylphosphate, tris(triethylenglycol)phosphate and diphenylphosphite are especially preferred.

Further, according to the invention mixtures of compound I with one or more of the following examples of compound II are particularly preferred (Formula II, X=N): Trioctyl-, triisooctyl-, trilauryl, tridecyl-, tridodecyl-, triisododecyl-, tritridecyl-, tripentadecyl-, trioleyl, tristearyl-, triphenyl-, trikresyl-, tris-nonylphenol, tris-2,4-t-butyl-phenyl-, tricyclohexylamine, also amines with a composition R1', R2', R3'=independent, the same or different: methyl, ethyl, n-propyl, iso-propyl, n-butyl, 2-butyl, iso-butyl, tert-butyl, n-pentyl, isopentyl, neo-pentyl, tert-pentyl, hexyl, heptyl, n-octyl, iso-octyl, 2,2,4-trimethylpentyl, nonyl, decyl, dodecyl, n-dodecyl, cyclopentyl, cyclohexyl, cycloheptyl, methylcyclohexyl, o-tolyl, p-tolyl, m-tolyl, xylyl, ethylphenyl, mesityl, phenyl, benzyl are suitable, as well as R1', R2', R3', R4'=H, R5'=Cl, or R1', R2', R3', R4'=H, R5'=Br.

Mixtures of compound I with one or more of the following examples of compound II of formula II are according to the invention preferred (X=Si): R1', R2', R3'=independent, the same or different: methyl, ethyl, n-propyl, iso-propyl, n-butyl, 2-butyl, iso-butyl, tert-butyl, n-pentyl, isopentyl, neo-pentyl, tert-pentyl, hexyl, heptyl, n-octyl, iso-octyl, 2,2,4-trimethylpentyl, nonyl, decyl, dodecyl, n-dodecyl, cyclopentyl, cyclohexyl, cycloheptyl, methylcyclohexyl, o-tolyl, p-tolyl, m-tolyl, xylyl, ethylphenyl, mesityl, phenyl, benzyl, R4'=O, OH, methanolate, ethanolate, n-propanolate, iso-propanolate, n-butanolate, 2-butanolate, iso-butanolate, tert-butanolate, n-pentanolate, iso-pentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclo-pentanolate, cyclohexanolate, cycloheptanolate, methylcyclohexanolate, glycolate, glycerate, pinacolate neopentylglycolate, vinylalcoholate, propargylalcoholate, 2-ethyl-1-hexanolate; or R1'and/or R2'=methyl, ethyl, n-propyl, iso-propyl, n-butyl, 2-butyl, iso-butyl, tert-butyl, n-pentyl, isopentyl, neo-pentyl, tert-pentyl, hexyl, heptyl, n-octyl, iso-octyl, 2,2,4-trimethylpentyl, nonyl, decyl, dodecyl, n-dodecyl, cyclopentyl, cyclohexyl, cycloheptyl, methylcyclohexyl, o-tolyl, p-tolyl, m-tolyl, xylyl, ethylphenyl, mesityl, phenyl, benzyl, R2', R3', R4'=independent, the same or different: O, OH, methanolate, ethanolate, n-propanolate, iso-propanolate, n-butanolate, 2-butanolate, iso-butanolate, tert-butanolate, n-pentanolate, iso-pentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclo-pentanolate, cyclohexanolate, cycloheptanolate, methylcyclohexanolate, glycolate, glycerate, pinacolate neopentylglycolate, vinylalcoholate, propargylalcoholate, 2-ethyl-1-hexanolate; or R1'=methyl, ethyl, n-propyl, iso-propyl, n-butyl, 2-butyl, iso-butyl, tert-butyl, n-pentyl, isopentyl, neo-pentyl, tert-pentyl, hexyl, heptyl, n-octyl, iso-octyl, 2,2,4-trimethylpentyl, nonyl, decyl, dodecyl, n-dodecyl, cyclopentyl, cyclohexyl, cycloheptyl, methylcyclohexyl, o-tolyl, p-tolyl, m-tolyl, xylyl, ethylphenyl, mesityl, phenyl, benzyl, R2', R3', R4'=O, OH, methanolate, ethanolate, n-propanolate, iso-propanolate, n-butanolate, 2-butanolate, iso-butanolate, tert-butanolate, n-pentanolate, iso-pentanolate, neo-pentanolate, tert-pentanolate, 2-methyl-1-butanolate, hexanolate, heptanolate, n-octanolate, iso-octanolate, 2,2,4-trimethylpentanolate, nonanolate, decanolate, dodecanolate, n-dodecanolate, cyclopentanolate, cyclohexanolate, cycloheptanolate, methylcyclohexanolate, glycolate, glycerate, pinacolate neopentylglycolate, vinylalcoholate, propargylalcoholate, 2-ethyl-1-hexanolate; or R1', R2', R3', R4'=independent, the same or different: O, OH, methanolate, ethanolate, n-propanolate, iso-propanolate, n-butanolate, 2-butanolate, iso-butanolate, tert-butanolate, n-pentanolate, iso-pentanolate, neo-pentanolate, tert-pentanolate, 2-methyl-1-butanolate, hexanolate, heptanolate, n-octanolate, iso-octanolate, 2,2,4-trimethylpentanolate, ndnanolate, decanolate, dodecanolate, n-dodecanolate, cyclopentanolate, cyclohexanolate, cycloheptanolate, methylcyclohexanolate, glycolate, glycerate, pinacolate neopentylglycolate, vinylalcoholate, propargylalcoholate, 2-ethyl-1-hexanolate. Especially preferred according to the invention are mixtures with the following examples of compound II: Isobutylisopropyl dimethoxysilan, diisopropyl dimethoxysilan, diisobutyldimethoxysilan, dicyclopentyl dimethoxysilan, n-propyltrimethoxysilan, isobutyl-sec-butyl dimethoxysilan, cyclohexylisobutyl dimethoxysilan, cyclo-pentylisobutyl dimethoxysilan, di-sec-butyl dimethoxysilan, dicyclohexyl dimethoxysilan, isobutylmethyl dimethoxysilan.

Mixtures of compound I with one or more of the following examples of compound II of formula II are according to the invention preferred (X=Cl or Br or I, with m=1): R1'=NH$_4$, Li, Na, K, Rb, for m=2: R1'=Cs, Mg, Ca, Sr, Ba, Zn for m=3: R1'=B, Al, Sc, Y, for m=4: R1'=Ti, Zr, Hf.

Also, mixtures of compound I with one or more of the following examples of compound II of formula III are according to the invention preferred, such as: NaClO$_2$, KClO$_2$, $HClO_2$, $HClO_3$, $KClO_3$, $NaClO_3$, $HClO_4$, $NaClO_4$, $KClO_4$, and, particularly preferred, NaCl, $AlCl_3$, KCl, NaBr, KBr, $NaClO_4$ and $KClO_4$ and their respective hydrates.

Moreover, mixtures of compound I with one or more of the following examples of compound II of formula III are according to the invention preferred (X=S): $Na_2SO_4$, $K_2SO_4$, $MgSO_4$, $CaSO_4$, $SrSO_4$, $BaSO_4$, $Al_2(SO_4)_3$, $NaAl(SO_4)_2$, $NH_4Al(SO_4)_2$, $KAl(SO_4)_2$ and their hydrates, particularly preferred are $Al_2(SO_4)_3$, $NaAl(SO_4)_2$, $NH_4Al(SO_4)_2$.

The molar ratio of compound I to compound II may by advantage be 1:0.001 to 1:200, preferred is a ratio of 1:0.01 to 1:20.

The composition of compound I and/or compound II may contain suspension agents or solvents to improve reaction kinetics and yield.

The invention further provides a process for the continuous or batchwise catalysis of esterification, transesterification, polyesterification, polytransesterification reactions of an alcohol and an acid or acid derivative, e.g. an ester, anhydride or halogenide, characterized by employing a catalytic composition as defined above.

This process may include the steps:
Preparation of a reaction mixture containing a polyvalent alcohol and an acid or ester with at least two carboxy groups.
Addition of catalytic composition according to the invention.

At least two catalytic compounds I and II may be added to the reaction mixture in isolated form, as solid, dissolved in a suitable solvent, as a liquid or as suspension.

The employed carboxylic acid may be a monocarboxylic acid, di- or polycarboxylic acid. Among dicarboxylic acids, carboxylic acids containing at least two carboxyl groups, dicarboxylic acids such as e.g. terephthalic acid and/or 2,6-naphthalenedicarboxylic acid, isophthalic acid, 1,4-cyclohexane dicarboxylic acid, 1,6-naphthalene dicarboxylic acid, 4,4-bisphenyl dicarboxylic acids, adipic acid, phthalic acid, alkane dicarboxylic acids, halogen derivates of the mentioned dicarboxylic acids for example tetrabromo phthalic acid, and copolymers of the mentioned dicarboxylic acids or the esters of the mentioned carboxylic acids for example dimethyl terephthalate, bis(hydroxyethyl) terephthalate, 2,6-dimethyl naphthalate, 1,6-dimethyl naphthalate are particularly preferred.

The alcohols employed in the process according to the invention may be mono-, di- or polyvalent.

As di- or polyvalent alcohols, alcohols such as ethylene glycol, 1,3-propanediol, 1,4-butanediol and/or 1,4-cyclohexanedimethanol, di-, triethylene glycol, polyglycols with a molecular weight below 1000 or neopentyl glycol, are particularly preferred.

Further, recycled polyester material might be used as co/monomer within the process based on the invention.

The inventors have shown that compound II, bearing a heteroatom as such neither catalyzes the esterification, nor transesterification, nor the polycondensation reaction. Surprisingly, an unexpected synergism between the metal catalyst (compound I) and the heteroatom compound (compound II) was found. The catalytic activity of selected systems of compound I can be increased according to the invention by approx. 50%.

According to the invention, the polycondensation is catalyzed and accelerated by a new compound system. It has been shown that in comparison to conventional catalytic systems less amounts of catalyst and stabilizer lead to comparable results. Furthermore, even high-viscous polyesters can be manufactured in a direct process in by far shorter polycondensation times. The novel mixtures according to the invention are further hydrolysis resistant and may be added either during the esterification phase and/or the precondensation phase as an active composition.

The catalytic composition of the invention shows a lower toxicity in comparison with conventional catalytic systems.

The preferred metal concentration of the catalytically effective metal compound (compound I) is 0.1 to 500 ppm (as Sn), in particular 10-200 ppm (as Sn) in relation to the acid or ester to be reacted.

The preferred concentration of the heteroatom containing compound (compound II) is 0.0001 ppm (as compound) to 1%, in particular 10-200 ppm in relation to the acid or ester to be reacted.

Particularly preferred is a process for a polyesterification reaction as defined above, characterized by reacting a dicarboxylic acid or a dicarboxylic acid derivative with a divalent alcohol.

Particularly preferred derivatives of mono-, di-, or polycarboxylic acids are esters or halogenides.

In the process of the invention hydroxycarboxylic acids such as p-hydroxybenzoic acid, salicylic acid, lactic acid, glycol acid or preferredly, derivatives thereof such as esters or ethers, and their co-polyesters with dicarboxylic acids and/or diols as described above may be reacted to the respective polyesters.

As a further compound a polyfunctional alcohol can be added to the reaction mixture. The polyfunctional alcohol, such as pentaerythritol can be added favored in a concentration of 0-500 ppm, in particular 50 ppm. The alcohol can be added together with compound I or separately, simultaneously, before or after, latest during the precondensation of the polyester. No influence on the effect of the other compounds occurs in this case.

The compounds I and/or II used for the production of polyester can be added during the period before the beginning of the esterification and/or transesterification until shortly before the end of the polycondensation, favored during the esterification and/or transesterification or before the precondensation.

A solvent or suspending agent may be added to compound I and/or compound II.

As solvents or suspending agents for the compounds I and/or II a mono-, di- or polyvalent alcohol such as e.g. an alkanediol may be employed. Preferred are 1,2-ethanediol, 1,3-propanediol, 1,4-butanediol, 2,2-dimethylpropan-1,3-diol.

The same solvent and/or suspending agent may be employed during manufacturing of the catalytic composition and said esterification, transesterification, polyesterification or polytransesterification reaction.

Alternative to this, also a different solvent and/or suspending agent may be employed during manufacturing of the catalytic composition and said esterification, transesterification, polyesterification or polytrans-esterification reaction.

Moreover, a solvent or suspending agent may be employed in the manufacturing step of the catalytic composition being selected from the group of mono-, di- or polyvalent alcohols that is reacted in said esterification, transesterification, polyesterification or polytransesterification reaction.

Further an organic liquid may be employed as solvent or suspending agent for the catalytic composition that is indifferent with respect to the polyester production process. Indifferent organic liquids are e.g. alkanes, cycloalkanes or benzene derivatives (for. example benzene, toluene, xylenes).

Also water or a mixture of water with an alcohol or a polyvalent alcohol is suited as solvent and/or suspending agent according to the invention.

Further additives for a color correction such as cobalt salts or organic dyes or pigments might be added to the reaction mixture, usually in amounts of 0.00001-5% by weight with respect to the acid or ester to be reacted.

Subject of the invention are further polycondensation products, produced by the described process of esterification, transesterification, polyesterification, polytransesterification with the use of the catalytic compositions according to the invention.

Furthermore, subject of the invention are polyester for bottles, films, foils, yarn, molded padding, resins for powder coatings and technical synthetic materials, obtainable by the process according to the invention.

The polyester available by the process according to the invention shows comparable qualities for the processability in comparison with conventional polyesters for example catalyzed by antimony. In comparison with usual high-viscous melt polymerisations, resins produced with the compounds described in the invention show a relatively low content of acetic aldehyde. In particular the polyesters synthesized with the process according to the invention show a narrow molecular weight distribution, a high translucency and give a polymer with a high, desired blue shift. A polymer of high viscosity is, unlike the state of the art using Sb catalysts, obtained without difficulty.

In the case of the inventive use of compound I with $R1=X-R^4$ the organotin catalyst is incorporated into the polymer by the means of an ester bond, that means the organotin species can only be released out of the polymer resin by its total destruction.

The polymers, produced with catalysts based on the invention show a high blue shift (negative b-values; color values are determined by using the CIE-Lab 100 color system with spectral reference beam color measuring instrument LUCI 100, Dr. Lange).

Polyesters, produced according to the invention employing a catalytic composition according to the invention show less by-products such as acetic aldehyde in polyethylene terephthalate (PET) in comparison with conventional techniques.

The polyesters produced according to the process described in the invention are made by esterification or transesterification with the use of the composition of compound I and/or compound II described in the invention and optionally subsequent polycondensation.

Preferred polyesters according to the invention are a) polyethylene terephthalate (PET), containing 0.1-10 mass % diethylene glycol and 0-10 mass % of isophthalic acid, 2-hydroxyisophthalic acid, p-hydroxyisophthalic acid, 2,6-naphthalene dicarboxylic acid and/or 1,4-cyclohexane dimethanole as co-monomer; b) polyester for powder coatings mainly poly-2,2-dimethylpropyl-1,3-terephthalate; c) polypropylene terephthalate (PPT); d) polyester polyols as for example polydiethyleneglycol terephthalate; e) polybutylene terephthalate (PBT); f) polynaphthalene terephthalates (PNT), g) polyethylene naphthalate (PEN).

The following examples further illustrate the invention without, however, limiting the invention. Unless otherwise indicated, parts and percentages relate to the weight, as in the remainder of the description.

EXAMPLES

Example 1

Preparation of Catalytic Active Mixtures of Compound I and Compound II:

Apparatus:
100 ml round bottom flask, magnetic stirrer, rotary evaporator.

Starting Materials, Quantities:

| | | |
|---|---|---|
| butyltin tris[neodecanoate] | 68.44 g | [0.10 mol] |
| a) triphenylphosphine | 26.23 g | [0.10 mol] |
| b) triphenylphosphite | 31.03 g | [0.10 mol] |
| c) triphenylphosphinoxide | 27.83 g | [0.10 mol] |
| d) tributylphosphite | 25.03 g | [0.10 mol] |

Preparation:
The heteroatom compound II, dissolved in xylene (ethanol in the case of triphenylphosphine oxide) was given into the round bottom flask and stirred for 15 min. Butyltin tris[neodecanoat] dissolved in 50 ml xylene or ethanol, respectively was added to the mixture by the means of a tap funnel and stirred for an additional hour. The catalytic active system was obtained after removal of the solvent under reduced pressure.

Analysis:
$^{119}$Sn-NMR
$^{31}$P-NMR
catalyst system e)

Apparatus:
250 ml three necked round bottom flask, tap funnel, magnetic stirrer, water separator, rotary evaporator.

Starting Materials, Quantities:

| | | |
|---|---|---|
| monobutyltin oxide | 20.88 g | [0.10 mol] |
| neodecanoic acid | 34.6 g | [0.20 mol] |
| triphenylphosphine | 26.23 g | [0.10 mol] |

Synthesis:
Monobutyltin oxide was dissolved in 150 ml xylene, triphenylphosphine, dissolved in 50 ml xylene and neodecanoic acid were added within 10 min. The mixture was heated under reflux until the water formation stops. The product was obtained after filtration and removal of the solvent under reduced pressure.

Example 2

Catalyst Test by Synthesis of a Resin for Powder Coatings:

Starting Materials, Quantities:

| | | |
|---|---|---|
| terephthalic acid | 83.07 g | [0.50 mol] |
| neopentylglycol (2,2-Dimethyl-1,3-propandiol) | 104.15 g | [1.00 mol] |
| catalyst: | 0.05% [m/m] calculated as Sn. | |

Synthesis:

Catalyst, neopentyl glycol and terephthalic acid were given into a 250 ml three-necked round bottom flask. The mixture was heated to a maximum by the means of a heating jacket, the reaction water is distilled off and the amount formed is metered.

The reaction time equals the time between the first water formation and the "clear point" of the reaction.

Example 3

Catalyst Test by Synthesis of a Resin for Powder Coatings with Physical Mixtures of Monobutyltin Oxide, Triphenylphosphine and Triphenylphosphite:

Starting Materials, Quantities:

| terephthalicacid | 83.07 g | [0.50 mol] |
|---|---|---|
| neopentylglycol (2,2-Dimethyl-1,3-propandiol) | 104.15 g | [1.00 mol] |
| catalyst: | f) 0.165 g monobutyltin oxide, 0.207 g triphenylphosphine | |
|  | g) 0.165 g monobutyltin oxide, 0.245 g triphenylphosphite | |

Synthesis:

Catalyst, neopentyl glycol and terephthalic acid are given into a 250 ml three-necked round bottom flask. The mixture is heated to a maximum by the means of a heating jacket, the reaction water is distilled off and the amount is metered.

The reaction time equals the time between the first water formation and the "clear point" of the reaction.

Table 1 shows the acceleration of the reaction time in the described resin synthesis with the mixtures of (comparative) examples 1a, 1b, 1c, 1d, 1e and 1f, 1g in comparison with the uncatalized reaction or with monobutyltinoxide (0.05% [m/m]) as catalyst.

Example 4

Polycondensation of bis(2-hydroxyethyl) terephthalate (BHET):

Experimental Method:

Polycondensation equipment 1 (glass equipment) for the melt polycondensation of BHET Tempering-bath (salt bath), polycondensation vessel (glass), screw mixer (glass), vacuum pump, pressure gauge As a polycondensation equipment, a round glass flask with round bottom was used, (internal diameter 2.6 cm, and 35 cm height, described in T. Johnson, Chem. Fibers International 46 (1996) 280; 49 (1999) 455). A horizontal vapor outlet was integrated into the upper third of the flask wall. A further extension tube near the bottom of the vessel allowed sampling from the polymer melt. The stirrer was a glassware screw mixer, reaching down to the ground (1.8 cm diameters). The mixer was operated with a rotation speed of 100 $min^{-1}$ and intermixed the melt with axially downward direction.

25.4 g (0.1 mol) BHET was filled into the polycondensation vessel, the catalyst (5 to 200 ppm as metal) was added and the vessel locked. Then the polycondensation vessel filled with the reaction mixture was evacuated three times and rinsed with dry nitrogen before it was immersed in the tempering-bath. The bath temperature was preset so that the desired internal temperature of 280° C. was reached in the polycondensation vessel. After the reaction mixture was melted, the stirrer was started and the vessel evacuated within 15 min onto a vacuum of $2 \times 10^{-1}$ mbar. The time of the first formation of glycol at the wall of the glass was regarded as to. The attainable final pressure for this equipment of approximately 4 to $5 \times 10^{-2}$ mbar, was reached after approx. 1 h experimental time, depending on the progress of the polycondensation. Through the sampling device samples could be taken by means of a VA steel wire, maintaining a nitrogen counterflow. At the end of the reaction up to 5 g could be taken from the vessel for further analysis. During the polycondensation, an average sampling required one minute, from break-

TABLE 1 reaction time of the mixtures a-g.

| catalyst (0.05% tin) | Sn-content [%] | volume H₂O [ml]: | | | | | | | | | | | | [min] time | remarks |
|---|---|---|---|---|---|---|---|---|---|---|---|---|---|---|---|
| | | 15 min | 30 min | 45 min | 60 min | 75 min | 90 min | 105 min | 120 min | 135 min | 150 min | 165 min | 180 min | | |
| without catalyst | | | | | 1 | | 1 | | 2 | | 3 | | 4 | 300 | aborted |
| triphenylphosphine | 0.05 | | | | 3 | | 4 | 4.5 | | | | | | 300 | aborted |
| monobutyltin oxide | 0.05 | | | | 9 | | 14 | | | | 23.5 | | | 155 | clear, colorless |
| monobutyltin trineo-decanoate | 0.05 | 2.5 | 4 | 5.5 | 7 | 9.5 | 11 | 13 | 15 | 17 | 18.5 | 21 | 22 | 180 | hazy, colorless |
| a | 0.05 | 3.5 | 6 | 9 | 11 | 14 | 16 | | | | | | | 100 | clear, colorless |
| b | 0.05 | 2.5 | 7 | 9 | 12 | 15 | 17 | | | | | | | 100 | clear, colorless |
| c | 0.05 | 2 | 6 | 9 | 13 | 15 | 18 | | | | | | | 97 | clear, colorless |
| d | 0.05 | 4 | 8 | 12 | 16 | 19 | | | | | | | | 85 | clear, colorless |
| e | 0.05 | 5 | 8 | 12 | 16 | 18 | | | | | | | | 60 | clear, colorless |
| f | 0.05 | | 8 | | 14 | | 16 | | | | | | | 100 | clear, colorless |
| g | 0.05 | 4 | 6 | 8 | 10 | 14 | 14 | 16 | 16 | | | | | 120 | clear, colorless | ing the vacuum to re-applying the vacuum. At the end of the polycondensation sampling was done within two minutes after aerating the vacuum.

PET Characterization

The determination of the intrinsic viscosities was performed as follows:

The relative solution viscosities $\eta_{rel}$ for PET were determined in phenol (3 parts)/dichlorobenzene (2 parts) mixtures using 0.5 percent solutions at 25° C. The conversion of the relative solution viscosities into the intrinsic viscosity [η] was done according to BILLMEIER.

$$\eta_{intr} = \frac{1}{4} \frac{\eta_{rel} - 1}{c + 3/4} \times \frac{\ln \eta_{rel}}{c}$$

From the intrinsic viscosities (IV) the average molecular weights Mn (number average) as well as the degrees of polymerization $P_n$ were calculated. For PET applies: Mn=(1000× IV)$^{1.5186}$; Pn=Mn/192.

The absolute viscosities were measured using the viscosimeter AVS 250 and the tempering-unit CT 1450 of Schott Geräte GmbH. Comparison measurements between different laboratories gave matching results.

The color values were determined using the CIE-LAB-Farbsystem (color system) by the spectral reference beam color measuring instrument LUCI 100, Dr. Lange.

The device STA 625 of Polymer Laboratories was used for TG and DSC-measurements.

The COOH end groups were determined by potentiometric titration of a cresol solution of the polymers with diluted aqueous NaOH.

BHET and the catalyst were introduced into the reaction vessel and rinsed well with nitrogen.

The reaction vessel was placed into the salt bath. Recording of reaction time started now. Within 15 min the pressure was lowered from 100 mbar to 0.09 mbar. At the end of the reaction a pressure of 0.04 mbar was reached.

The following table 2 shows the results of the polycondensation experiments for the catalyst e in comparison to Sb- and Ti-based catalysts (table 3). Criteria of the catalyst activity are the attainable molar mass in specific time periods, the increasing influence of the thermal degradation, recognizable by the flattening of the $P_n$-t-function as well as the color values of the polyester. The amount of the evolved ethanal (acetaldehyde) that directly correlates with the degree of thermal ester group cleavage is a further essential criterion of the catalyst suitability. The color values in the tables show the discoloration of the product, the a-values representing green/red-gradients and the b-values representing blue/yellow-gradients, Negative a-values correspond to green, negative b-values correspond to blue gradients. Blue shift is favored technologically.

TABLE 2

Polycondensation of BHET with catalyst e.

| time [min] | Sn [ppm] | $\eta_i$ | COOH [µeq/g] | $M_n$ [g/Mol] | $P_n$ | color values using the CIE-LAB-system | | |
|---|---|---|---|---|---|---|---|---|
| | | | | | | L | a | b |
| 30 | 123 | 0.2764 | 16 | 5104 | 26 | 34.19 | −0.15 | −0.14 |
| 60 | 123 | 0.5216 | 14 | 13386 | 69 | 33.84 | −0.28 | 0.46 |
| 90 | 123 | 0.7152 | 19 | 21616 | 112 | 37.73 | −0.44 | 1.05 |
| 120 | 123 | 0.8399 | 24 | 27588 | 143 | 36.54 | −0.63 | 1.78 |

TABLE 3

Polycondensation of BHET with Sb and Ti catalysts.

| Catalyst | temperature [° C.] | time [min] | catalyst conc. [ppm] | $P_n$ |
|---|---|---|---|---|
| antimony triacetate | 270 | 30 | 190 | 25 |
| antimony triacetate | 270 | 60 | 190 | 45 |
| antimony triacetate | 270 | 90 | 190 | 65 |
| antimony triacetate | 270 | 120 | 190 | 85 |
| antimony triacetate | 270 | 150 | 190 | 100 |
| antimony triacetate | 270 | 180 | 190 | 115 |
| antimony triacetate | 280 | 30 | 190 | 30 |
| antimony triacetate | 280 | 60 | 190 | 55 |
| antimony triacetate | 280 | 90 | 190 | 75 |
| antimony triacetate | 280 | 120 | 190 | 95 |
| antimony triacetate | 280 | 150 | 190 | 115 |
| antimony triacetate | 280 | 180 | 190 | 135 |
| tetrabutyl titanate | 280 | 30 | 20 | 45 |
| tetrabutyl titanate | 280 | 60 | 20 | 65 |
| tetrabutyl titanate | 280 | 90 | 20 | 85 |
| tetrabutyl titanate | 280 | 120 | 20 | 105 |
| tetrabutyl titanate | 280 | 150 | 20 | 125 |
| tetrabutyl titanate | 280 | 180 | 20 | 150 |

The comparative investigations for the catalytic activity of the selected tin compounds show that no noteworthy thermal decomposition is to be expected within 2 h of polycondensation time at temperatures of 280° C. Therefore it is absolutely possibly to synthesize even higher molecular weight polyethylene terephthalates by prolongation of the polycondensation time.

All examined tin compounds proved as high-activity catalysts for the polycondensation of BHET, which show significantly higher activity than stibious compounds. Their polytransesterification activity is superior to titanium alkoxides and titanium chelates. If required, they can be employed also in higher concentrations.

The invention claimed is:

1. A catalytic composition useful for esterification, transesterification and polycondensation reactions consisting of butyltin tris[neodecanoate] and one phosphorus-containing compound selected from the group consisting of a triphenylphosphine, a triphenylphosphite, a triphenylphosphinoxide, and a tributylphosphite.

2. The composition of claim 1, employing a concentration of the butyltin tris[neodecanoate] in the range of 0.1 to 1% by weight, with respect to the acid or ester to be reacted.

3. The composition of claim 2, employing a concentration of the one phosphorus-containing compound in the range of 0.0001 ppm to 1% by weight, with respect to the acid or ester to be reacted.

* * * * *